US006593582B2

United States Patent
Lee et al.

(10) Patent No.: US 6,593,582 B2
(45) Date of Patent: Jul. 15, 2003

(54) PORTABLE DIGITAL LIDAR SYSTEM

(75) Inventors: Hyo Sang Lee, Silver Spring, MD (US); In Heon Hwang, Columbia, MD (US); Coorg R. Prasad, Silver Spring, MD (US)

(73) Assignee: Science & Engineering Services, Inc., Burtonsville, MD (US)

( * ) Notice: Subject to any disclaimer, the term of this patent is extended or adjusted under 35 U.S.C. 154(b) by 29 days.

(21) Appl. No.: 09/852,782

(22) Filed: May 11, 2001

(65) Prior Publication Data

US 2002/0175294 A1 Nov. 28, 2002

(51) Int. Cl.[7] .............................................. G01N 21/17
(52) U.S. Cl. .................................. 250/458.1; 250/341.1
(58) Field of Search ........................... 250/458.1, 459.1, 250/461.1, 338.1, 338.5, 339.01, 339.06, 339.07, 341.1

(56) References Cited

U.S. PATENT DOCUMENTS 5,373,160 A * 12/1994 Taylor ..................... 250/338.5

OTHER PUBLICATIONS

"The 440 nm Fluorescence Band of Cultured Bacteria in Solution and on Surfaces", Philips J. Hargis, Jr., 1998 Scientific Conference on Obsuration and Aerosol Research, Aberdeen Proving Ground, MD 1998.

"Short Range Biological Standoff Detection System (SR–B-SDS)", William Suliga, et al., Fourth Joint Workshop on Standoff Detection for Chemical and Biological defense, pp. 265–274, Sep. 15, 1998.

"Single Shot Fluorescence Spectra Of Single Micron Sized Particles For The Characterization Of Biological Aerosols", Yong–le Pan, et al., Paper #CWF6, p. 254, CLEO, May 26, 1999.

"Results of Multispectral UV Fluorescence Lidar Field Test Measurements at Dugway Proving Ground, Utah and White Sands Missile Range, New Mexico," Philip J. Hargis, Jr., et al., 2000 MASINT Biological Warfare Science and Technology Symposium, Long Beach, CA, Jan. 10–13, 2000.

"Exploratory Development Of A Remote NBC Detector Using Ultraviolet Technology", William K. Bischel, et al., SRI Int. Report CRDC–CR–84102, (17 pp.), Aug., 1984.

"Development Of IR and UV Lidar Systems For Standoff Detection Of Airborne Biological Materials", Mark W. Wilson, et al., Final Report, Contract DAAA15–91–C–0138, STC Technical Report, 2674, Jan. 1993.

(List continued on next page.)

Primary Examiner—David Porta
Assistant Examiner—Timothy J. Moran
(74) Attorney, Agent, or Firm—Oblon, Spivak, McClelland, Maier & Neustadt, P.C.

(57) ABSTRACT

A light detecting and ranging system and method for detecting airborne agents in which the system includes a laser which provides laser pulses of at least two wavelengths, a transmitter which transmits the laser pulses, a receiver which receives both elastically backscattered signals from airborne agents and fluorescence signals from the airborne agents, a common telescope which both focuses a laser beam transmission of the laser pulse from the transmitter to a far field and receives the elastically backscattered signals and the fluorescence signals from the far field, a digital detection system having at least one of a backscatter optical detector which detects the elastically backscattered signals and a fluorescence optical detector which detects the fluorescence signals from the airborne agents.

Figure 1:
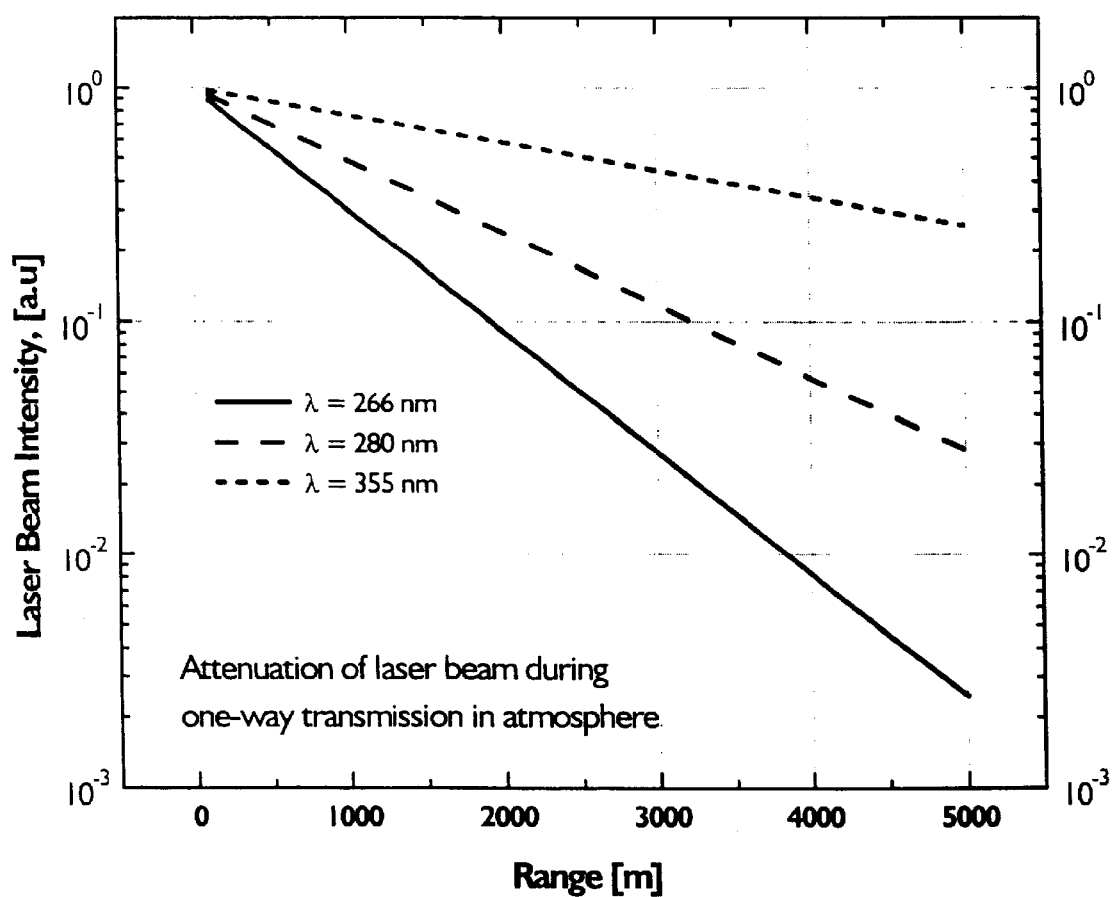
Figure 2A:
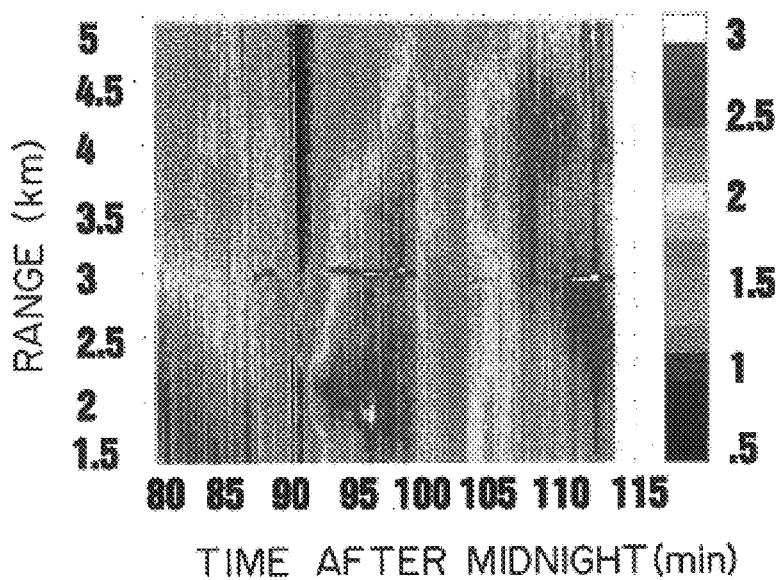
Figure 2B:
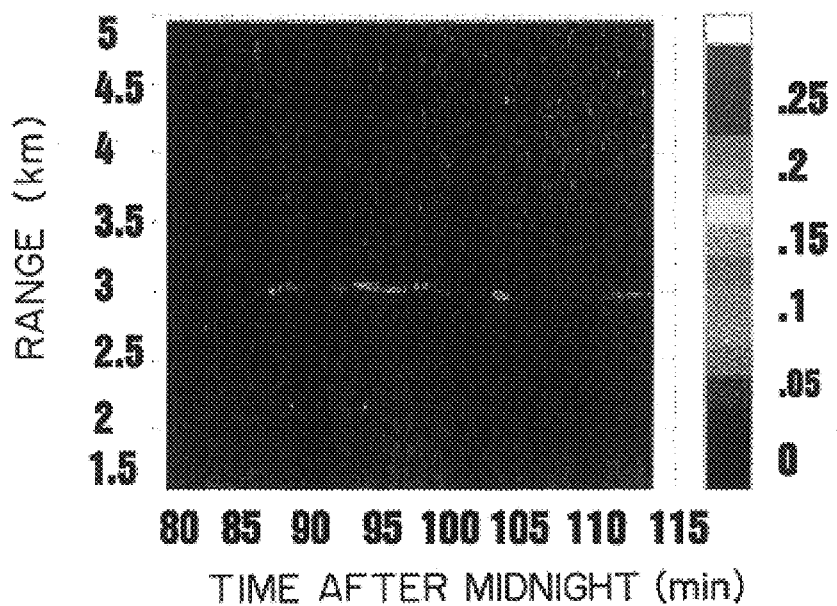
Figure 2C:
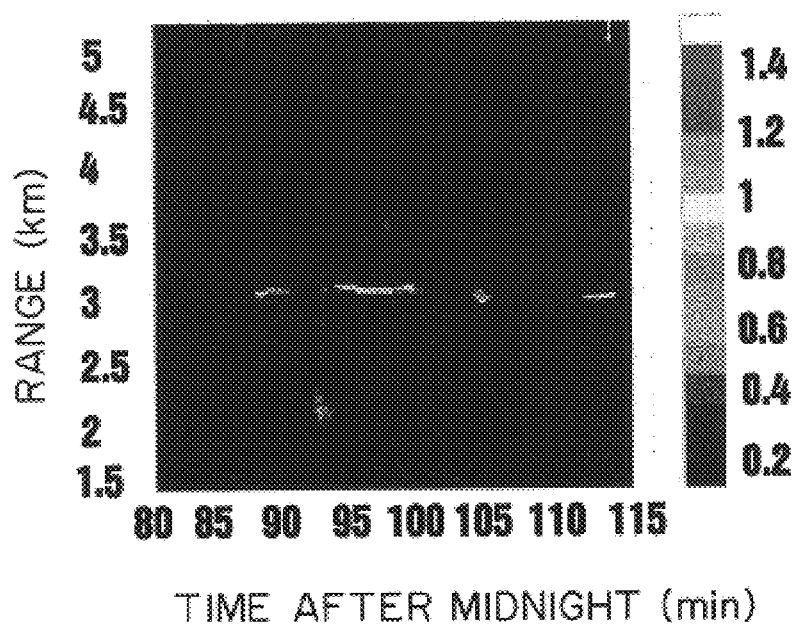
Figure 2D:
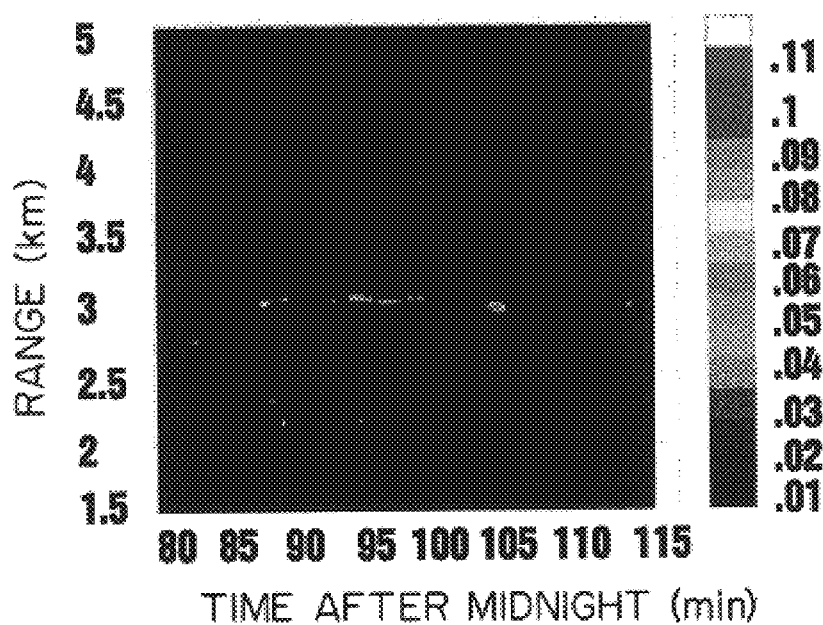

67 Claims, 12 Drawing Sheets (2 of 12 Drawing Sheet(s) Filed in Color)

OTHER PUBLICATIONS

Fluorescence Particle Counter for Detecting Airborne Bacteria and Other Biological Particles, Ronald G. Pinnick, et al., Aerosol Science and Technology, 23:653–664, 1995.

"Laser Remote Sensing Fundamentals and Applications", Raymond M. Measures, Krieger Publishing Company, 1992.

"Principles of Fluorescence Spectroscopy", Joseph R. Lakowicz, Plenum Press, NY, pp 341–363, 1984.

"Conditional–Firing Aerosol– Fluorescence Spectrum Analyzer For Individual Airborne Particles With Pulsed 266–Nm Laser Excitation", Gang Chen, et al., Optics Letters, vol. 21, No 16, Aug. 15, 1996.

Advances in Atmospheric Remote Sensing with Lidar, pp 7–10, A.Ansmann, Ed., Springer Variag, Berlin, 1997.

"High Sensitivity Eye–Safe Lidar for Biological Aerosol Detection, "I.H. Hwang, et al., Proceedings of the Joint Workshop on Standoff Detection for Chemical and Biological Defense, pp. 297–303, 1998.

"Active Range Gated Spectometric Standoff Detection and Characterization of Bioaerosols", Jean–R. Simard, et al., Proceedings of SPIE, vol. 3707, Apr., 1999, pp 116–128.

"U.S. Army Soldier and Biological Chemical Command Counter Proliferation Long Range—Biological Standoff Detection System (CP LR BSDS)", Lawrence A. Condatore, Jr., et al., Proceedings of SPIE, vol. 3707, Apr., 1999, pp 188–196.

"Biological Standoff Detection—The Army Program", Bruce W. Jezek, et al., Joint Workshop on Standoff Detection for Chemical and Biological defense, pp. 7–12, Oct. 1998.

"Ground–Based Differential Absorption Lidar System For Day Or Night Measurements Of Ozone Throughout The Free Troposphere", Profitt, et al, Applied Optics, 36, #12, pp. 2568–2585, Apr., 1997.

"Measuremnets Of Fluorescence Cross–Sections Of Biological Agent Simulants", Sci Conf. on Chemical & Biological Defense Res., Aberdeen Proving Ground, MD., #159, Oct., 1997.

UV Fluorescence Lidar Detection of Bioaerosols, Atmospheric Propagation and Remote Sensing III, Steven D. Christesen, et al, The International Society for Optical Engineering, vol. 2222, pp. 228–237, Apr. 5–7, 1994.

Detection of Bioaerosols Using Multiwavelenght UV Fluorescence Spectroscopy, Y.S. Cheng, et al., Aerosol Science and Technology 30:186–201, 1999.

* cited by examiner

Transceiver Optical Module

Laser 54

Legend

| | |
|---|---|
| 1-6 | Lenses |
| 7 | Near-IR beam |
| 8 | Visible beam |
| 9,15 | Polarizing beam splitters |
| 10-14 | Dichroic mirrors |
| 17-20 | Filters |
| 21-30 | Mirrors |
| 31-33 | Pinholes for field stops |
| 34 | Telescope focal point |
| 35 | Broadband Dichroic mirror |
| 36, 37 | Depolarizars |
| 38 | UV aerosol beam |
| 39 | UV beam |
| 40-43 | Focusing Lenses |
| 54 | Laser |

TABLE I

| Laser Energy | 1.5 mJ/pulse @ 355 nm; 0.35 mJ @ 532 and 1 mJ @1064 nm; 2 kHz |
|---|---|
| Transmitter | Eyesafe: 10cm beam 1.5 mJ @ 355 nm. 30 cm beam: 70μJ @ 532nm; 200 μJ @ 1064nm; |
| Receiver Telescope | 30 cm Cassegrain, Commercial |
| Detectors | 440 nm : PMT; 532 nm & 1064 nm: Si APD SPCM |
| Optical Filters | $\Delta\lambda$=20nm, 0.2nm, 0.5nm @ 440, 532 and 1064nm |
| Aerosol Sensor Scan | Complete ±60° scans; Scan speeds 1 to 5° /sec |
| Range | Max Range = 20 km aerosol; 7 km fluorescence |
| Fluorescence Sensor | Stop & Stare; Integration time = 10 s to 1 min |
| Fluoresc. Sensitivity | $10^3$ p/l @ 2 km; $1.25 \times 10^4$ p/l @ 4km S/N = 2 |
| Size, Weight, Power | ~ 7 cft (32" x 24" x16"); ~ 130 lbs; ~ 750 W |

FIG. 8

TABLE 2

| Flourescent Species | Flour. CS cm2/sr.nm. particle | Exctn. Wavelength | Flour. Wavelength | Particle size |
|---|---|---|---|---|
| BG Vegetative | $5 \times 10^{-14}$ [1] | 280nm | 320nm | 5-10 μm |
| BG Spores | $5 \times 10^{-15}$ [1] | 280 | 310 | 1-2 μm |
| Bm | $2 \times 10^{-14}$ [1] | 280 | 318 | 5-10 μm |
| BG Vegetative | $3.5 \times 10^{-15}$ [2] | 266 | 320 | dry aerosol |
| BG aerosol | $1.6 \times 10^{-14}$ [2] | 266 | 310 | wet aerosol |
| Bm spores | $3 \times 10^{-14}$ [3] | 280 | 318 | liq. suspnsn |

1. Stephens

Table 3. Maximum Permissible Energy: Eye-Safe Laser Transmitter

| Wavelength (nm) | 1060 | 532 | 355 |
|---|---|---|---|
| MPE µJ/cm² (for a single pulse) | 5 | 0.5 | $10^6$ |
| MPE µJ/cm² (for a 2kHz laser) Exposure duration | 0.42 (10 s) | .107 (0.25 s) | $8 \times 10^4$ (10 s) |
| Transmitter Dia (cm) | 30* | 30* | 8 |
| Eye-safe† laser energy µJ/pulse | 272 | 69 | $4.2 \times 10^6$ |

† Repetitive pulse exposure: $(N)^{-1/4}$ law; * Central blockage 8.8 cm

FIG. 10

PORTABLE DIGITAL LIDAR SYSTEM

BACKGROUND OF THE INVENTION

1. Field of the Invention

The present invention relates to a portable light detecting and ranging (LIDAR) system for long-range aerosol detection of biological weapon gas clouds. As such, the system can be used to provide early warning for field personnel, providing the necessary time for personnel to prepare for the arriving gas cloud.

2. Discussion of the Background

Remote stand-off detection of chemical/biological (chem/bio) agents is considered to be a critical necessity in early warning systems enabling maximum survivability of personnel in the battlefield and other sensitive areas. Pulsed elastic backscatter lidar operating in the visible, as described by Lee, et al, "Micro Pulse Lidar for Aerosol & Cloud Measurement", *Advances in Atmospheric Remote Sensing with Lidar,* pp 7–10, A. Ansmann, Ed., Springer Verlag, Berlin, 1997, the entire contents of which are incorporated herein by reference, and near IR, as described by Condatore, et al, "U.S. Army Soldier and Biological Chemical Command Counter Proliferation Long Range—Biological Standoff Detection System (CP LR BSDS)", *Proceedings of SPIE,* Vol. 3707, 1999, the entire contents of which are incorporated herein by reference, have demonstrated the high sensitivity and long-range (up to 50 km) capability to detect aerosol clouds. Consequently, aerosol lidar is a chosen technique for long-range detection of bio-warfare aerosols. However, single wavelength aerosol lidars, as currently employed, do not provide discrimination between biological weapon (BW) agent aerosols and other natural or interferent aerosol clouds. The capability to differentiate can be augmented by using multiple wavelength and/or multiple polarization elastic scattering signatures. However, the elastic scattering technique lacks the required specificity for deterministic application of the data in the battle field.

Aerosol lidar is an ideal complement to uv fluorescence lidar, as demonstrated by Wilson, et al, "Development of IR and UV Lidar systems for standoff detection of airborne biological materials" Final Report, Contract DAAA15-91-C-0138, STC Technical Report, 1993, the entire contents of which are incorporated herein by reference, which discloses a UV laser that excites fluorescence from the biological constituents of the aerosol and measures the fluorescence signature of the biological constituents to provide specificity for discrimination between bio-aerosols and other naturally occurring or interfering aerosols. Since atmospheric absorption at UV wavelengths is high and fluorescence cross-section of the target particles is small, even the use of a high energy laser source with a large aperture telescope only enables conventional fluorescence lidar to achieve a range coverage of three to four kilometers. Jezek and Cannaliato, "Biological Standoff Detection", Joint Workshop on Standoff Detection for Chemical and Biological defense, pp. 26–30, October 1998, the entire contents of which are incorporated herein by reference, have been actively developing both long range and short range sensor systems. Long-range biological standoff detection system LR BSDS, as described in Condatore, et al, "U.S. Army Soldier and Biological Chemical Command Counter Proliferation Long Range—Biological Standoff Detection System (CP LR BSDS)", *Proceedings of SPIE,* Vol. 3707, 1999, the entire contents of which are incorporated herein by reference, is based on elastic scatter aerosol lidar. Short range biological standoff detection system SR BSDS, as described in Suliga, et al, "Short Range Biological Standoff Detection System (SR-BSDS)", *Fourth Joint Workshop on Standoff Detection for Chemical and Biological Defense,* Sep. 15, 1998, the entire contents of which are incorporated herein by reference, is based on fluorescence and aerosol lidar.

Current chem/bio defense detection systems can provide a rapid indication of a possible BW attack by utilizing multiple independent technologies to provide separate lines of data, which are less likely to be wrong at the same time, thus reducing false alarms. However, present technologies, owing to the complexity and laser power levels required for fluorescence and aerosol lidar, are limited in range and not well suited for an in-the-field, portable early warning detection system.

SUMMARY OF THE INVENTION

Accordingly, one object of the present invention is to provide an early warning detection system which can provide accurate detection of biological weapons at sufficient distance to provide an adequate response time.

Another object of the present invention is to integrate multiple analysis techniques into a detection system to reduce a probability of false alarms.

Still a further object is to provide a self-aligned detection system which improves reliability of the detection system in the field.

A further object of the present invention is to provide a digital detection system which can by multiplexing improve the signal-to-noise ratios and the detected signals.

These and other objects are achieved in a lidar system including a laser which provides laser pulses of at least two wavelengths, a transmitter which transmits the laser pulses, a receiver which receives both elastically backscattered signals from airborne agents and fluorescence signals from the airborne agents, a common telescope which both focuses a laser beam transmission of the laser pulse from the transmitter to a far field and receives the elastically backscattered signals and the fluorescence signals from the far field, a digital detection system having at least one of a backscatter optical detector which detects the elastically backscattered signals and a fluorescence optical detector which detects the fluorescence signals from the airborne agents.

Indeed, the lidar system of the present invention maximizes the signal-to-noise ratio (SNR), thus maximizing the range capability for a given SNR. An acceptable criterion for the confident detection of BW agent aerosol in the atmosphere is for the signal-to-noise ratio of the lidar signal to be about four. In addition to photon shot noise generated by the laser scattered light falling on the detector, a detection system itself can contribute to the noise. In a conventional lidar system, where analog detection technique is used, the noise depends on the detector dark noise together with the signal shot noise, i.e., the noise in the associated amplifier and the detection bandwidth. The bandwidth of a lidar system is determined by the desired spatial resolution of the lidar measurement. For example, a 15 m spatial resolution requires at least 5 MHz bandwidth. The minimum signal required for an analog lidar system to successfully measure an aerosol is determined by the detector dark current and the bandwidth. Thus, in the analog lidar design approach of the present invention, increasing the measurement range requires increasing the signal, which normally implies a high-energy laser and a large telescope for collecting the signal. For the BSDS system previously discussed, a laser energy>100 mJ, and a telescope receiver size of 65 cm dia. is utilized.

In contrast, the portable digital lidar (PDL) system of the present invention is based on a different approach, i.e., digital detection, where the detection noise is minimized so that a much lower signal level is adequate to yield the required SNR. Digital detection utilizes photon-counting which generates digital pulses for every photon that is detected and is not affected by the bandwidth or the amplifier noise. In one embodiment of the present invention, a Geiger mode avalanche photodiode (APD) detector is utilized with low signal induced noise. Other than the photon shot noise, the only noise source in digital detector is the detector dark count noise, which is about three orders of magnitude smaller than the dark current noise in an analog detector.

Hence, digital detection system is capable of detecting signals nearly a thousand times smaller than analog detection. Thus, the laser energy for the fluorescence excitation can be reduced to ~1 mJ, allowing compact diode-pumped solid state (DPSS) lasers to be utilized which have the performance stability and the rugged configuration necessary for battlefield operation along with low power consumption. As a consequence, the laser size and cost are reduced by nearly a factor of ten. Further, the DPSS lasers can operate at high pulse repetition frequency (PRF) of a few kHz without significantly increasing cost or size. Averaging multiple shot data improves the SNR (as the square root of the number of pulses). By averaging over many thousands of shots, the useful range of the lidar is extended as the SNR at the extended range becomes acceptable within a few seconds. While the SNR of an analog lidar detector can be improved by signal averaging, increasing the PRF of a analog-suitable laser (e.g., a 100 mJ laser with a repetition rate of 30 Hz) can be relatively expensive and difficult.

The PDL system of the present invention is equipped with a scanner to cover a wide angle (±60°) for simultaneously monitoring multi-wavelength elastic scattering and laser-induced fluorescence from aerosols. Tracking of cloud and aerosol packets by rapidly scanning over a wide field of view allows the wind direction and speed to be obtained continuously. The concept of using a single $3^{rd}$ harmonic Nd:YAG laser and tapping the residual 1.06 $\mu$m, 532 nm wavelength outputs for aerosol elastic scatter not only results in a compact lidar system but provides other additional benefits, as discussed next.

First, wavelengths greater than 1.5 $\mu$m have been used in other lidars (e.g., LR and SR BSDS) to render the lidar systems eye-safe. However, the 1.5 $\mu$m laser is a complex system requiring the 1.06 $\mu$m Nd:YAG output to be down shifted in an optical parametric oscillator OPO. Also, commonly available 1.5 $\mu$m detectors are not sufficiently sensitive; hence special detectors are needed, adding to the cost and complexity of the sensing systems. On the other hand, since the laser energy required for the PDL of the present invention is small, the laser beams at both 532 nm and 1.06 $\mu$m can be made eye-safe by expanding the transmitted laser beam. The expansion of the transmitted laser beam is achieved by utilizing a telescope as both a transmitter and a receiver. Internal analysis of the aerosol backscatter signals have shown that a 20 km range is achieved with such an eye-safe lidar with a minimal averaging time of less than 0.5 sec, so that rapid scanning is feasible.

Second, the particle sizes for naturally occurring aerosols range from 0.2–0.8 $\mu$m while the particle size for bio-aerosols range from 2–10 $\mu$m. Of the two chosen laser wavelengths, 532 nm is roughly equal to, and 1.06 $\mu$m is larger than, the natural aerosols, whereas the two chosen wavelengths are both smaller than the bio-aerosols. Hence, a differentiation between the naturally occurring aerosols and the bio-aerosols is possible by comparing the scattered signals at these two wavelengths. According to the present invention, combining the scattering differences with a 355 nm excited bio-fluorescence which has the potential for discrimination between man-made and naturally occurring bacteria provides an early and confirmatory warning system for the detection of a bio-aerosol presence.

Third, another innovation of the PDL system of the present invention is a common transmitter/receiver telescope system. Since the transmitter and receiver utilize a common optical conjugate point, both the transmitted beam and the receiver field-of-view stay aligned at all times, making the system immune to misalignment resulting from the displacement of telescope optics resulting from either vibration or thermal distortions. A single telescope which serves as both a transmitter and a receiver results in a compact, low-cost, and light system. Further, according to the present invention, internal scattering interferences can be minimized through the use of spatial and spectral filters.

Thus, the PDL lidar sensor of the present invention is well-suited for biological standoff detection. The sensor addresses the requirements of high sensitivity and autonomous operation capability, eye-safety, and the ability to operate during the day for long-range detection. Importantly, these attributes are complemented with small size, rugged packaging, low power and maintenance requirements, and low cost.

BRIEF DESCRIPTION OF THE DRAWINGS

The patent or application file contains at least one drawing executed in color. Copies of this patent or patent application publication with color drawing(s) will be provided by the Office upon request and payment of the necessary fee. A more complete appreciation of the invention and many of the attendant advantages thereof will be readily obtained as the same becomes better understood by reference to the following detailed description when considered in connection with the accompanying drawings, wherein:

FIG. 1 is a diagram showing at the three wavelengths (266, 280 and 355 nm) the reduction in the laser beam intensity due to scattering and absorption by atmospheric constituents as the laser beam travels to a target.;

FIG. 2 is a false color plot showing aerosol backscatter time-series data for both the visible and near-IR wavelengths;

FIG. 3 is an optical schematic of the lidar system of the present invention including a transceiver optical module and a transmitter/receiver telescope;

FIG. 3A is an optical schematic of the transceiver optical module of the present invention;

FIG. 4 is a schematic of a component layout for the lidar system of the present invention;

FIG. 5 is a diagram illustrating the calculated SNR for excitation at a wavelength of 266 nm;

FIG. 6 is a diagram illustrating the calculated SNR for excitation at a wavelength of 355 nm;

FIG. 7 is a diagram illustrating the SNR of the total signal from both atmospheric aerosols and a BG aerosol calculated using equation (1);

FIG. 8 depicts Table 1 showing typical parameters for the PDL system of the present invention;

FIG. 9 depicts Table 2 showing for a number of biological clouds and the average particle size the respective fluorescence cross sections and fluorescence peaks for a given excitation wavelength;

FIG. 10 depicts Table 3 showing the maximum permissible energy for eye-safe laser transmission;

DESCRIPTION OF PREFERRED EMBODIMENTS

Referring now to the drawings, wherein like reference numerals designate identical or corresponding parts throughout the several views, and more particularly to FIG. 1 thereof, FIG. 1 shows at three wavelengths (i.e., 266, 280 and 355 nm) the reduction in the laser beam intensity due to scattering and absorption by atmospheric constituents as the laser beam travels to a target. According to the present invention, the difference in the fluorescence between excitation at 266 nm and 355 nm is more than compensated by the difference in the atmospheric transmittance shown in FIG. 1. From the lidar signal considerations shown in FIG. 1, even with a 100-fold smaller fluorescence cross section, the 355 nm lidar is a preferred embodiment of the present invention.

In a fluorescence lidar, autofluorescence excited by a UV laser from biological cells is utilized to identify the fluorescing biological cells from other non-biological or naturally occurring particles. Naturally fluorescent aromatic amino acids residues which are the intrinsic constituents of nearly all proteins contribute to the fluorescence, as described in Lakowicz, "Principles of fluorescence spectroscopy", Plenum Press, NY, 1984, the entire contents of which are incorporated herein by reference. For the stand-off lidar field application, appropriate candidate UV lasers are fourth and third harmonic diode-pumped Nd:YAG laser, having wavelengths at 266 and 355 nm, respectively. In this excitation wavelength region, the fluorescent biomolecules are: amino acids—tryptophan, tyrosine, nicotinamide adenine dinucleotide compounds (NADH), and the flavins (riboflavin). The specificity of the spectral signatures from different BW agents is still under debate, see for example Simard, et al, "Active Range Gated Spectrometric Standoff Detection and Characterization of Bioaerosols", *Proceedings of SPIE*, Vol. 3707, 1999, the entire contents of which are incorporated herein by reference.

However, internal experiments of the present inventors have shown that excitation by 355 nm is preferable to that at 266 nm. Furthermore, recent results by Hargis, et al, "The 440 nm Fluorescence Band of Cultured Bacteria in Solution and on Surfaces," 1998 Scientific Conference on Obsuration and Aerosol Research, Aberdeen Proving Ground, MD 1998, and Hargis, et al, "Results of Multispectral UV Fluorescence Lidar Field Test Measurements at Dugway Proving Ground, Utah and White Sands Missile Range, New Mexico," 2000 MASINT Biological Warfare Science and technology Symposium, Long Beach, Calif., 2000, the entire contents of which are incorporated herein by reference, have also demonstrated that excitation at 355 nm has several advantages. One, the induced fluorescence at the 440 nm region is a robust indicator of biological material and is not affected by the growth media used for preparation of the bio-material. On the other hand, the 330 nm band fluorescence (arising mainly from tryptophan) is significantly changed by the growth media. Thus, the 440 nm band fluorescence can discriminate between man-made and naturally occurring bacteria. Also, the smaller atmospheric extinction at both the excitation (355 nm) and fluorescence (440 nm) wavelengths permits a longer range capability as compared to excitation at the 266 nm wavelength. Hence, while not limited to excitation at 355 nm, the PDL fluorescence lidar system of the present invention utilizes a compact diode-pumped Nd:YAG laser whose third harmonic (355 nm) is used for excitation of the 440 nm fluorescence band and whose residual outputs at the fundamental (1.064 $\mu$m) and second harmonic (532 nm) are available for aerosol lidar sensing.

To predict the performance of the fluorescence lidar and to choose an appropriate laser wavelength, the fluorescence cross-sections $\sigma_f$ for the aromatic amino acids, some of the bacterial BW agents (e.g., BG, BS, BT), as well as other potential candidates such as NADH, riboflavin, etc. have been studied. This study of the present inventors has yielded $\sigma_f$ values which are consistent within a factor of ten and at the present time, and the present invention utilizes the consistency of cross-sectional data information.

Bacterial spectral profiles, as described by Chen et al, "Conditional-firing aerosol-fluorescence Spectrum Analyzer for Individual Airborne Particles with Pulsed 266-nm Laser Excitation", *Optics Letters*, Vol. 21, No 16, Aug. 15, 1996; Pinnick, et al, "Fluorescence Particle Counter for Detecting Airborne Bacteria and Other Biological Particles", *Aerosol Science and Technology*, vol. 23, pp. 653–664, 1995; Stephens, "Measurements of fluorescence cross-sections of biological agent simulants" *Sci Conf. on Chemical & Biological Defense Res.*, Aberdeen Proving Ground, MD., #159, 1997; Wilson, et al, "UV Laser-induced fluorescence Test 1991" Report ERDEC TR-109, 1993, the entire contents of each reference are incorporated herein by reference, show a resemblance to the spectral profiles of tryptophan except that the wavelength of the peak for tryptophan is blue shifted by 20–30 nm from bacterial profiles. In addition, the fluorescence intensity at 450 nm is much lower (about 10% lower) than the fluorescence intensity at 350 nm for most of the bacteria except for *B. subtilis*.

Table 2 of FIG. 9 shows some of the fluorescence cross-sections reported in the literature. Considerable variation is found in the measured cross-sectional CS values as reported by different groups. Some of this variation arises due to differences in the excitation wavelength, the size and state of the agent particle, and the manner in which it is prepared, e.g., unsporulated or spore-separated, wet or dry aerosol, etc. Occasionally, the literature refers to bacteria BG (*bacillus globigii*) as *B. Subtilis*. One comprehensive set of measurements was performed by Bischel et al, "Exploratory development of a remote NBC detector using Ultraviolet technology", SRI Int. Report CRDC-CR-84102, 1984, the entire contents of which are incorporated herein by reference. Fluorescence cross-sections are sometimes given in per unit mass of the bio-aerosol instead of per particle. By knowing the size of the individual particles, an estimate the number density of these particles can be made and converted to a value per particle or a colony-forming unit (cfu). Taking the mean diameter of the particles as 5 $\mu$m, and that each particle on the average has 100 individual bacteria of a mass of $5\times10^{-13}$ gm each, an estimate for the particle count is about $2\times10^4$ particles/$\mu$g.

While the fluorescence cross-section data suggests that the appropriate excitation wavelength should be that which is best suited for tryptophan, i.e., 266 or 280 nm, the sharp increase in atmospheric attenuation at the shorter wavelengths allows consideration of using 355 nm excitation. As previously noted, the preferred wavelength for discrimination between natural and man-made bacteria or other biomolecules is the 355 nm wavelength. Specifically, the spectral fluorescence profiles from many different tryptophan containing bacteria were virtually identical for short UV ($\lambda$<295 nm) excitation so that it is not possible to distinguish one bacteria from another by the spectral signature. Similarly, there is no discernible difference between live and dead or spores and unsporulated bacteria. There are, however, measurable differences between micro-organisms that contain tryptophan (e.g., *E-coli,* BG, BT, MS, etc) and those that do not contain tryptophan (e.g., Mycotoxin). In addition, considerable variation in fluorescence is found depending on the way the bacteria was prepared (e.g., how the bacteria was washed, and which growth media was used). Meanwhile, the 440 nm fluorescence resulting from excitation at longer UV wavelengths ($\lambda$>310 nm) is undiminished by the presence or absence of the growth media and is not diminished but does depend on whether the bacteria has been washed or not.

Thus, according to the present invention, the 440 nm fluorescence is considered to be a robust and preferred indicator of biological, cultured material. Fluorescence at 440 nm can also arise as described in Pan, et al, "Single shot fluorescence spectra of single micron sized particles for the characterization of biological aerosols", Paper #CWF6, p. 254, CLEO 1999; and Pinnick, et al, "Fluorescence Particle Counter for Detecting Airborne Bacteria and Other Biological Particles", *Aerosol Science and Technology,* 23:653–664, 1995, the entire contents of each reference are incorporated herein by reference, from NADH, NADPH, NAD+, and flavins. The 440 nm fluorescence band of the bacteria is expected to be weak in naturally-occurring bacteria, while strong in cultured (man-made) bacteria. The 440 nm fluorescence band represents a way to distinguish man-made from naturally occurring bacteria, leading to the reduction of false alarms in remote stand-off detection instruments.

The wavelength for efficient excitation of fluorescence in bacteria and other bio-molecules is the 340–360 nm region. Hence, according to the present invention, the third harmonic of Nd:YAG laser at 355 nm can be utilized as an excitation source. Recent advances in diode-pumped solid state (DPSS) lasers together with the advances in nonlinear materials have lead to efficient harmonic frequency conversion UV lasers, e.g., frequency tripled (355 nm) and quadrupled (266 nm) diode-pumped Nd:YAG or Nd:YLF lasers with moderately high average powers (up to 5 W in UV) and PRF of 1 to 2 kHz are now commercially available. With these lasers, according to the present invention, the fundamental and second harmonic beams (0.532, and 1.06 $\mu$m) can be utilized for aerosol monitoring.

The appropriateness of these two wavelengths (0.532, and 1.06 $\mu$m) for the detection of bio-aerosols has been demonstrated in previous internal work, as described in Lee et al, "Micro Pulse Lidar for Aerosol & Cloud Measurement", *Advances in Atmospheric Remote Sensing with Lidar,* pp 7–10, A. Ansmann, Ed., Springer Verlag, Berlin, 1997; and Hwang, et al, "High Sensitivity eye-safe Lidar for Biological Aerosol Detection," Proceedings of the Joint Workshop on Standoff Detection for Chemical and Biological Defense, pp. 297–303, 1998, the entire contents of each reference are incorporated herein by reference. Further, as to be discussed later, simulation analysis has confirmed the appropriateness of 0.532, and 1.06 $\mu$m for the detection of bio-aerosols. A sufficient SNR can be obtained at a range up to 20 km for both wavelengths, with energies that are low enough to maintain an eye-safe, transmitted beam. Field experimental measurements by the present inventors of bio-simulant aerosols with a two-wavelength aerosol lidar showed that, in addition to excellent detection sensitivity, preliminary differentiation between several types of aerosols is also obtained.

FIG. 2 shows aerosol backscatter time-series data in the form of false color plots for both the visible and near-IR wavelengths. The x-axis variable is time and y-axis variable is range. The signal intensity is indicated by the color coding shown on the color bar. The two plots in FIG. 2 are raw data aerosol signals for a BG disseminated at 3 km, with the wind flowing perpendicular to the line of sight. Hence, the aerosol range is unchanged, and the intensity decays after the dissemination is stopped. A differential backscattering signal obtained from the ratio of the signals at the two wavelengths shows significant differences for different types of particles such as: BG, EH (*erwinia herbicola*), kaolin, and road dust. Hence, according to the present invention, preliminary differentiation between natural and disseminated aerosol clouds is made by utilizing this ratio.

Figure 3:
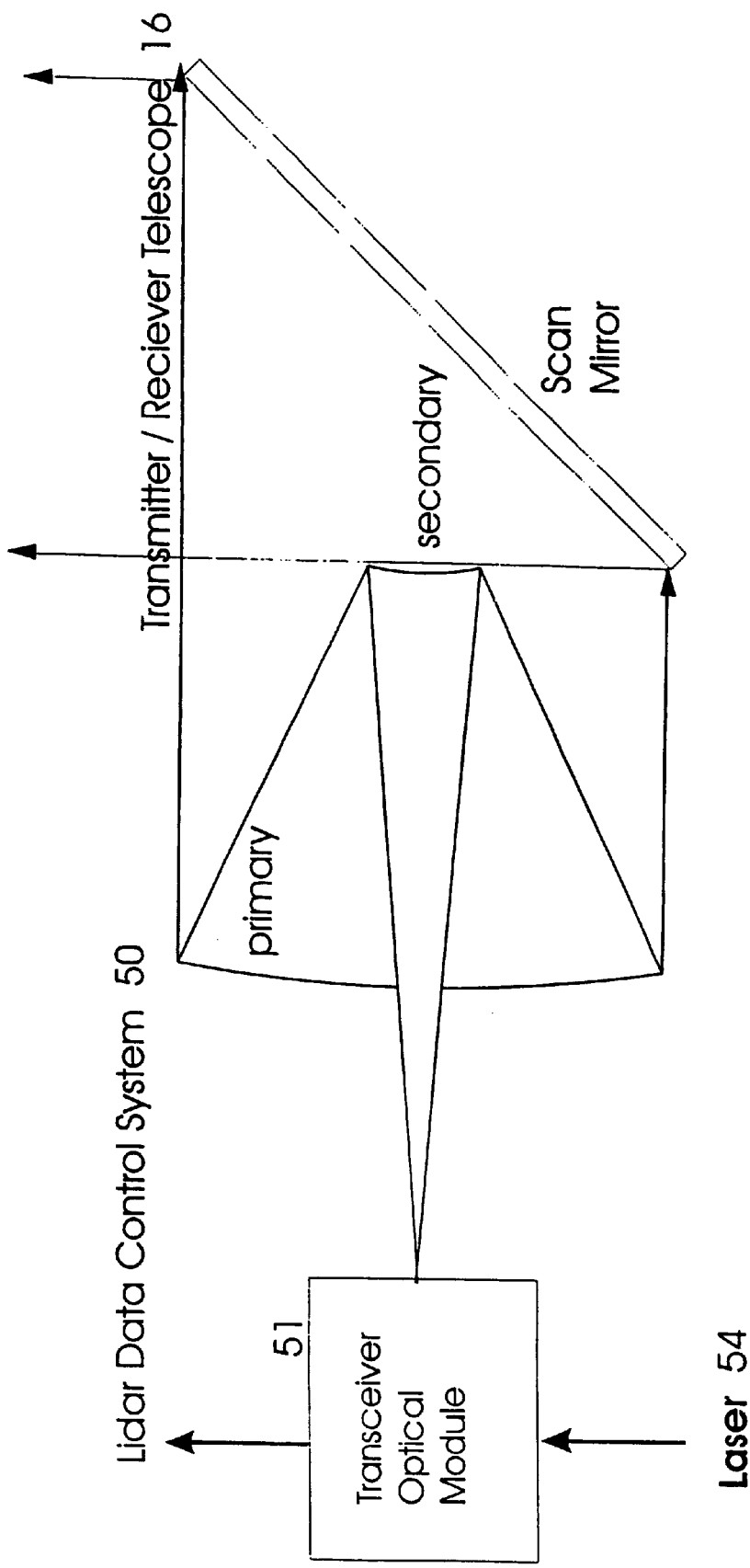
Figure 3A:
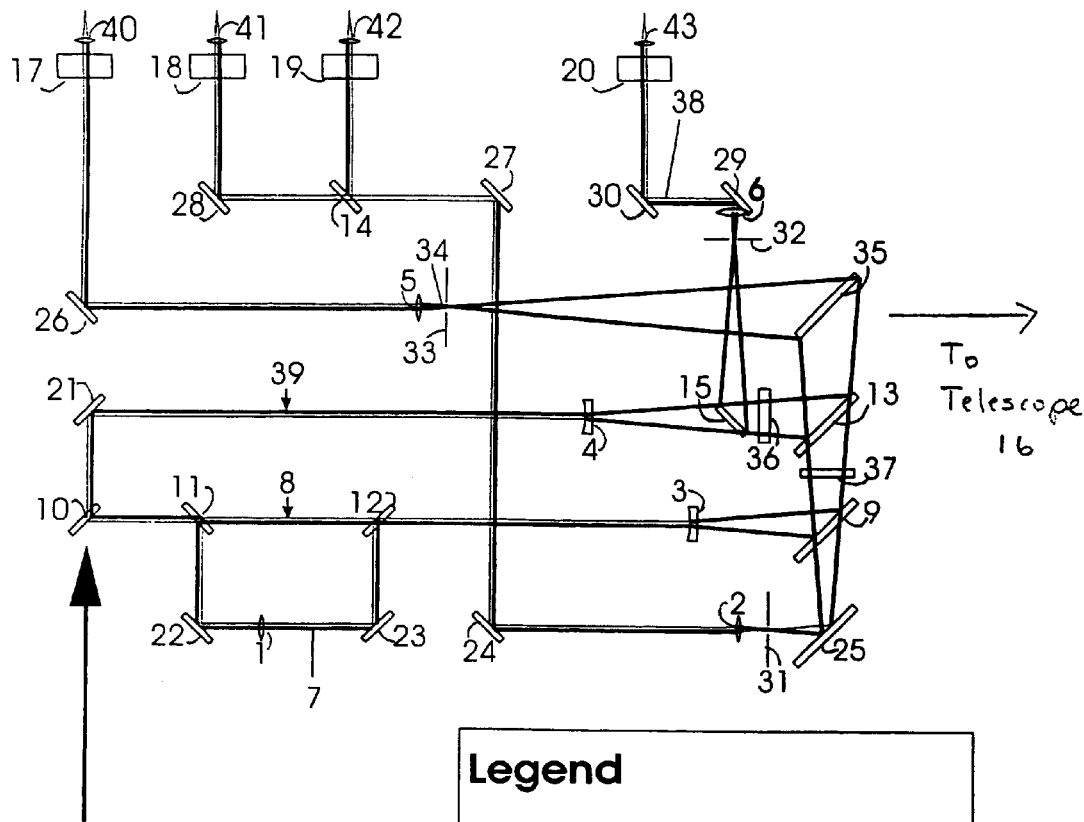
Figure 4:
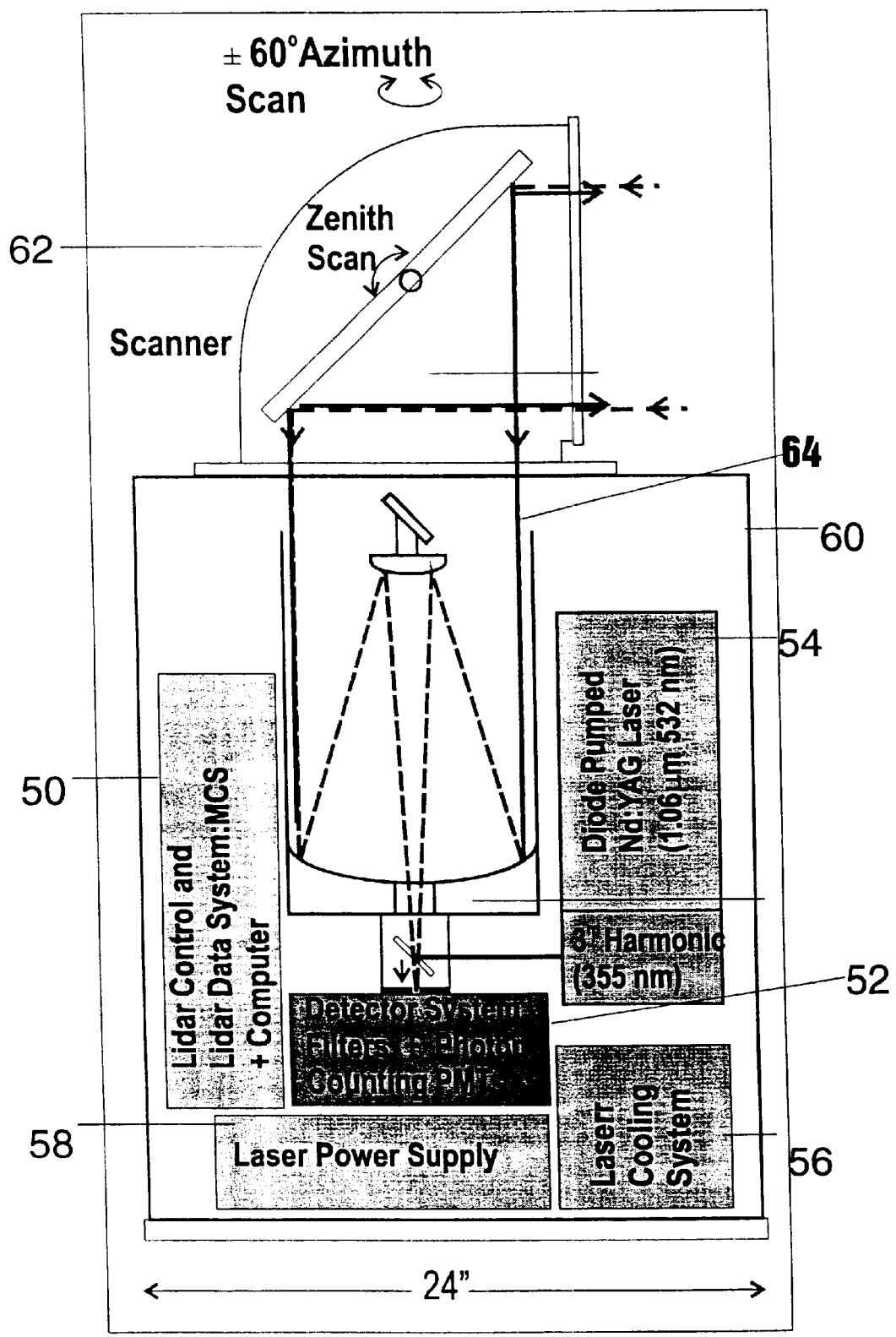

Accordingly, the lidar system of the present invention includes a transmitter, a receiver, a scanner, an electronics module for data acquisition, and a computer for lidar control, data display and data archival. FIG. 3 shows an optical schematic of the lidar system of the present invention including a transceiver optical module 51 and a transmitter/receiver telescope 16. FIG. 3A is an optical schematic of the transceiver optical module 51 of the present invention. FIG. 4 shows a component layout for the lidar system of the present invention. System parameters for the lidar system of the present invention are listed in Table 1 of FIG. 8.

As previously noted, recent advances in diode-pumped solid state DPSS lasers together with the advances in non-linear materials, have lead to efficient harmonic frequency conversion UV lasers, e.g., frequency tripled (355 nm) and quadrupled (266 nm) diode-pumped Nd:YAG or Nd:YLF lasers with moderately high average powers (up to 5 W in UV) and PRF of 1 to 2 kHz are now commercially available. With these lasers, the fundamental and second harmonic beams (0.532, and 1.06 $\mu$m) can also be utilized. FIG. 4 shows a diode pumped Nd:YAG laser 54 emitting 1.06 $\mu$m, 532 nm, and 355 nm laser light. The laser 54 is serviced by a cooling system 56 and a power supply 58.

All three laser wavelengths are appropriately beam-shaped using lenses 1–6 shown in FIG. 3A. Two transmitted beams, near-IR 7 and visible 8 are combined using a dichroic mirror 12 into a single beam, which is reflected by the polarizing beam splitter 9. The sensor utilizes six dichroic mirrors 10–14 and 35. An UV beam 38 is independently expanded by the lens 4 and passes through the polarizing beam splitter 15 before being joined to the other beams 7, 8 by one of the dichroic mirrors 13. The combined beam is expanded to the full size of telescope 16 and transmitted into the atmosphere as overlapping beams. The receiver subsystem includes the telescope 16 and four photodetectors 17–20, not shown are pre-detection relay optics, optical and electronic filters, power supplies, and gating electronics. The telescope 16 can be for example a compact Schmidt-Cassegrain 30 cm aperture commercial telescope with UV enhanced aluminium coated mirrors. According to the present invention, the telescope 16 transmits the overlapping laser beams and receives the backscattered and fluorescence signals. A transmitting vector is located co-axially on the receiver axis. The field stops (including components 31–33) at the focal point 34 of the telescope defines the transmitter optic axis and ensures that the receiver optic axis aligns collinearly regardless of the actual alignment of the rest of the telescope optics. Thus, according to the present invention, coaxial alignment of the transmitter and receiver axes is automatically assured at all time. Assurance of alignment can be an important feature for field operational. Therefore, the present invention can accommodate a significant level of mechanical vibration of the platform during measurement, as well as during transportation.

The small field stops 31–33 employed and the polarization filtering minimize laser light scattering. The depolarized return signal contains all three scattered components, and the fluorescence are separated by the dichroic mirror 35 with a broadband filter and passes through the field stops 31–33. Depolarizer or ¼ wave polarization rotators 36, 37 are used to implement the polarizing beam splitter. Different wavelength signals received in the return signal are separated by the dichroic mirror and then focused onto the respective photodetectors. Narrow band filters (not shown in FIG. 3A) spectrally centered at the laser wavelengths transmit the unshifted elastic backscattered radiation efficiently (T~40%) while rejecting the background solar radiation. A broadband filter (not shown in FIG. 3) centered at 440 nm is used for the fluorescence channel. A bandwidth of 10 nm for the broadband filter is adequate, according to the present invention. The broadband filter also provides a greater than $10^6$-fold rejection of the exciting radiation at 355 nm, and a rejection of longer wavelength daylight radiation, $\lambda$ greater than 450 nm.

According to the present invention, the solar background radiation reaching the detector is reduced by employing a telescope with a small field of view FOV and narrow band pass filters in the transmitting channels, thus enabling daylight aerosol lidar measurements. However, the background solar radiation coming through the wider bandwidth of the fluorescence channel at 440 nm can exceed the backscattered or fluorescent signals even for signals being reflected or generated nearby. Although the background can be separately determined and subtracted, the higher photon shot noise can degrade the measurement and in extreme cases restricts an operational range. However, since the viability of bacteria in bright sunlight is very small, bio-agent disseminations are expected to occur under conditions when no significant solar radiation is present. Thus, the PDL system of the present invention is well-suited for filed applications.

FIG. 4 shows the detection system 52 of the present invention. Si-based avalanche photodiodes APD and photo multiplier tubes PMTs are utilized for detectors 17–20 shown in FIG. 3. Typically, a Si-APD detector quantum efficiency is approximately 15% at 440 nm, greater than 50% at 532 and, and approximately 70% at 830 nm, and decreases to less than 3% at 1.06 $\mu$m. Quantum efficiency of conventional PMT is approximately 20% at 440 nm, and 10 to 15% over the visible, decreasing quickly for the infrared. All detector channels can, according to the present invention, utilize Geiger mode Si APD single photon counting modules. However, the fluorescence and the UV scatter signals utilize UV PMTs operating in a photon counting mode.

The field stop apertures 31–33 of the present invention limit the telescope FOV and provide geometric compression of signal for all channels, and prevent detector overloading from an initial scattered signal in the near field. The size of the aperture and the transmitted beam divergence serve to compress the dynamic range of the lidar signal. Furthermore, according to the present invention, the detectors can be gated off for a short period following the laser-pulse transmission to avoid an after-pulsing effect which can cause detector overload. An optical Q-switch (not shown in FIG. 4) can be applied in front of the detectors 17–20 to filter initial scattered light as well as near-field signals. Small portions of the three outgoing beams are collected for energy monitoring of the photo-diodes and signal normalization.

As shown in FIG. 4, the data acquisition system 50 of the present invention includes programmable multichannel scalers (MCS) directly connected to the detector modules. Range bins of the MCS are selectable between 100 $\mu$sec (e.g.

for 15 m range resolution) and 2 $\mu$sec (e.g. for 300 m range resolution). The data acquisition system 50 also includes a computer to control the laser operation, the gating of the detectors, acquisition of energy monitor data, and lidar signals. Time integration of the lidar return signals is performed by the MCS units and the averaged data is read at a predetermined rate by a processor in the MCS and transmitted to the computer.

According to the present invention, an effective algorithm for rapid analysis of the aerosol signals and identification of suspect aerosol clouds is incorporated in the computer for real-time operation applications. Upon confirming the presence of bio-particles in the aerosol cloud, an automatic alarm is generated. Further processing of the signal is done on the computer. The computer features real-time, range-intensity display of the signal data.

One issue with lidar systems is compliance with eye-safety regulations. One conventional method for complying with the laser eye-safety requirement utilizes infrared wavelengths beyond 1.6 $\mu$m, as described in Cannalito, "Biological Standoff Detection", Joint Workshop on Standoff Detection for Chemical and Biological defense, pp. 26–30, October 1998, the entire contents of which are incorporated herein by reference. However, such systems are bulky and expensive due to the high laser energy and special detectors that are required. According to the present invention, the eye-safety requirement is met by expanding the transmitted laser beams to the full aperture of the telescope so that the power density of the transmitted beams is reduced below the eye-safe limit. Table 3 of FIG. 10 lists the eye-safety criteria for laser exposure defined in terms of the maximum permissible exposure (MPE) for the naked eye according to the American National Standards Institute (i.e., ANSI Z136). The MPE for a pulse laser is based on the peak power of the pulse, while the MPE for a cw system concerns the total energy for an extended exposure period depending on the eye aversion, which is a fraction of a second for visible light and a few seconds for the UV and IR lasers.

The MPE for repetitive pulses in the visible wavelengths with a PRF of N is reduced from the MPE of a single pulse by a factor of $N^{-1/4}$. Since the reduction of MPE is a rather slow function of the pulse repetition rate while the average power increases linearly with the pulse repetition rate, the eye-safe lidar system of the present invention utilizes a high PRF low pulse energy laser transmitter which provides comparable average output power. The signal information content is linearly proportional to the average power when the noise contribution is properly filtered. Thus, according to the present invention, the laser beam upon expansion by the telescope 16 satisfies the ANSI eye-safety requirement.

To illustrate compliance with this standard, MPE values have been computed for the different laser beams. As an example, MPE value for a 532 nm single pulse is ~$5\times10^{-7}$ J/cm$^2$, which becomes $1.06\times10^{-7}$ J/cm$^2$ for 500 pulses (0.25 sec eye-blink response exposure of a 2 kHz laser) by the $N^{-1/4}$ law. Therefore, by expanding the beam in a 30 cm telescope, this expansion translates to a 69 $\mu$J pulse energy which satisfies the MPE requirement. For 355 nm, the MPE value is ~1 J/cm$^2$ for a single pulse, thus producing a 4.2 J/cm$^2$ for 10 sec exposure of a 2 kHz laser according to the $N^{-1/4}$ law. Even if the $N^{-1/4}$ law is not applicable to the UV exposure, the direct cumulative 1 sec exposure (2000 pulses) at 1.5 mJ amounts to energy density of only 4.3 mJ/cm$^2$, for the 30 cm transmitter, which is well below the MPE of 1 J/cm$^2$.

One possible concern for biological defense applications is that a 532 nm wavelength utilized for aerosol detection may easily be seen (i.e. a 532 nm wavelength is green). But, the extremely low beam energy density and the small beam divergence at the telescope make the beam nearly invisible except when directly staring into the transmitter. If, however, the green light compromises the security of the sensor, one alternative, according to the present invention, is to use an elastic backscatter from 355 nm together with the 1.06 μm near-IR (invisible) wavelengths for two wavelength aerosol measurements. Such an alternative will reduce the range, but would otherwise retain the same attributes as the 532 nm operation.

Hence, the lidar system of the present invention provides a portable digital fluorescence and aerosol lidar system to provide an early warning system. The system provides aerosol cloud detection at a range up to a 20 km range and clear discrimination of bio-aerosols at an adequate range of ~6 km. The digital fluorescence and aerosol lidar sensors in the lidar system provide further differentiation between natural and artificially-made clouds at sufficient range for adequate warning. For example, assuming an average wind speed of ~20 km/hr, the 20 km range capability for detecting aerosol clouds translates to a one hour early warning period, and a 18-minute warning period after confirmation at 6 km range. Further, differentiation between different cloud types can be accomplished by using the aerosol lidar data to determine the physical characteristics of the clouds such as the extent, rate of spread, and decay.

Furthermore, the present invention integrates fluorescence and aerosol lidar into a single portable system that is nearly an order of magnitude smaller in weight and size, and an order of magnitude less costly than the high energy BSDS systems previously discussed. By using multiple independent technologies providing separate lines of data, which are less likely to be wrong at the same time, false alarm rates are reduced. By complementing the lidar system of the present invention with a suite of in-situ identification sensors, such as sample identification units, immuno-diagnostic and mass spectrometric devices which can be deployed upon early warning by the lidar system of the presence of a bio-warfare agent, the requirement of bio-warfare agent detection and identification are amply satisfied.

To facilitate the analysis and comparisons of the lidar system of the present invention to discriminate between natural and man-made aerosols, the bio-aerosol simulant, *bacillus globigii* (BG) has been considered. For a lidar with a laser pulse energy $E_L$, at wavelength $\lambda_L$, and duration $\tau_p$, the energy $E_s(R)$ collected at wavelength $\lambda_s$ by a telescope of area A from a layer of thickness $\Delta R=c\Delta T/2$, (with $\tau_p<\Delta T$), at a range R=ct/2 at a time t after the laser pulse is transmitted is given according to Measures, "Laser Remote Sensing Fundamentals and Applications", Krieger Publishing Company, 1992, the entire contents of which are incorporated herein by reference, by:

$$E_s(\lambda_s, R) = \eta\phi(R)\beta(\lambda_s)E_L(\lambda_L)\frac{A\Delta R}{R^2}\exp\left[-\int_0^R[\alpha(\lambda_L)+\alpha(\lambda_s)]dz\right] \quad (1)$$

where $\eta$=system optical efficiency, $\phi(R)$=geometric overlap function, $\beta(\lambda_s)$=volume back-scattering coefficient for aerosol lidar or the volumetric fluorescence cross-section for fluorescent lidar, $\alpha(\lambda_L)$ and $\alpha(\lambda_s)$=the attenuation coefficient at the wavelengths $\lambda_L$ and $\lambda_s$.

The performance simulations of the aerosol and fluorescence PDL lidar were performed using an internal lidar simulation model. Equation (1) was employed for calculating the signal received at the detector and the resulting SNR. PDL system parameters are given in Table 1 of FIG. 8. Mid-latitude standard atmosphere was assumed, and the atmospheric transmittances at the laser and the fluorescence band wavelengths were calculated with the MODTRAN (Ontar Corp.) program for a number of atmospheric visibility values. To accurately factor in the extinction due to absorption by ozone, the standard mid-latitude lower troposphere ozone concentration profile of Profitt, et al, *Applied Optics,* 36, #12, pp. 2568–2585, 1997, the entire contents of which are incorporated herein by reference, was employed.

Calculations for three kinds of biological aerosols were performed: *Bacteria subtilis, E coli* and a naturally occurring pollen from Stinging Nettle trees. As mentioned above, the directly-measured fluorescence-scattering cross-sections of Stephens, "Measurements of fluorescence cross-sections of biological agent simulants" *Sci Conf. on Chemical & Biological Defense Res.,* Aberdeen Proving Ground, MD., #159, 1997, Wong, et al, "UV Laser-induced fluorescence Test 1991" Report ERDEC TR-109, 1993; Wilson, et al, "Development of IR and UV Lidar systems for standoff detection of airborne biological materials" Final Report, Contract DAAA15-91-C-0138, STC Technical Report, 1993; Bischel, et al, "Exploratory development of a remote NBC detector using Ultraviolet technology", SRI Int. Report CRDC-CR-84102, 1984, the entire contents of which are incorporated herein by reference, were utilized in the calculations. Fluorescence cross-sections for the bio-aerosol particulates were integrated over the spectral bandpass filter bandwidth and corrected for system optical efficiency i.e., $\eta.\beta_s$ values were taken to be ~$7.3\times10^{-8}$, $5.9\times10^{-8}$, and $5.1\times10^{-10}$ cm$^2$/$\mu$g, for *B. subtilis* (spores), *E Coli* and Stinging nettle pollen. An excitation at 280 nm was initially used in the calculation.

Excitation at longer wavelengths (340 to 360 nm) showed exciting new results and appears to have a greater potential for discrimination than the 266 or 280 nm excitation. The fluorescence cross-sections for excitation at 355 nm are not available yet for the three species considered here. However, internal laboratory measurements of the present inventors indicate that the cross-sections for 355 nm are approximately a tenth of that for excitation at 266 nm. Comparisons with other reported values for other bacteria show this is a reasonable assumption.

FIGS. 5 and 6 show the calculated SNR for excitation at 266 nm and 355 nm, respectively. The simulant aerosol is taken to be a BG disseminated at 1 mg/m$^3$ concentration. This concentration corresponds to $2\times10^4$ particles/ltr. The fluorescence cross-section is conservatively taken to be $7.9\times10^{-9}$ m$^2$/mg at 266 nm and $7.9\times10^{-10}$ m$^2$/mg at 355 nm excitation. (In recent measurements, the cross-sections for BG spores have been reported to be as large as $2.8\times10^{-8}$ m$^2$/mg for 266 nm and $2.8\times10^{-9}$ m$^2$/mg for 355 nm). Comparing FIGS. 5 and 6, the signal decays much faster with range (FIG. 5) for 266 excitation even though the fluorescence cross-section is ten times larger, since the atmospheric attenuation is much stronger at 266 nm than that for 355 nm excitation. according to the present invention, enhancements are possible by increasing the laser energy and the PRF without considerably changing the size or cost of the system.

The minimum detectable concentrations are determined by taking the $SNR_{min}$=4. For 266 nm, excitation at 5 km range, a minimum detectable concentration of $2\times10^4$ ppl is estimated, whereas for 355 nm, even at 7 km the minimum detectable concentration is better than $1\times10^4$ ppl. This analysis demonstrates that the performance of the PDL system of the present invention can provide performance adequate for standoff detection of a BWA cloud at a distance required for military operations.

The computed performance of the lidar system of the present invention was calculated. Equation (1) is valid for the aerosol elastic scattered lidar signal, i.e., $\lambda_s=\lambda_L$, and $\beta(\lambda_s)$=volume aerosol back-scattering coefficient, $\alpha(\lambda_s)$=extinction coefficient at the wavelengths $\lambda_s$. The volumetric backscattering coefficient $$\beta = \beta_M + \beta_A + \beta_{BWA} = \frac{3}{8\pi} \cdot \alpha_M + \rho_A \cdot \alpha_A + \beta_{BWA} \qquad (2)$$

is the sum of contributions from atmospheric molecules $\beta_M$ and aerosols $\beta_A$, in addition to the BW agent $\beta_{BWA}$ backscattering. The shape of molecular scattering phase function, as described in Measures, "Laser Remote Sensing Fundamentals and Applications", Krieger Publishing Company, 1992, the entire contents of which are incorporated herein by reference, determines the relation between the molecular backscattering coefficient $\beta_M$ and the corresponding extinction coefficient, $\alpha_M$, as $\beta_M=(3/8\pi)\alpha_M$. The ratio $\rho_A$, of aerosol backscattering coefficient to the aerosol extinction coefficient, $\rho_A=\beta_A/\alpha_A$, is not a constant and depends on the composition, size and shape of the aerosol particles. For most atmospheric aerosols, $\rho_A$ varies from 0.012 to 0.05/sr, and we have taken a value of 0.03/sr for our calculations. $\alpha_M$ and $\alpha_A$ are obtained from the MODTRAN program for the given atmospheric conditions.

Figure 7:
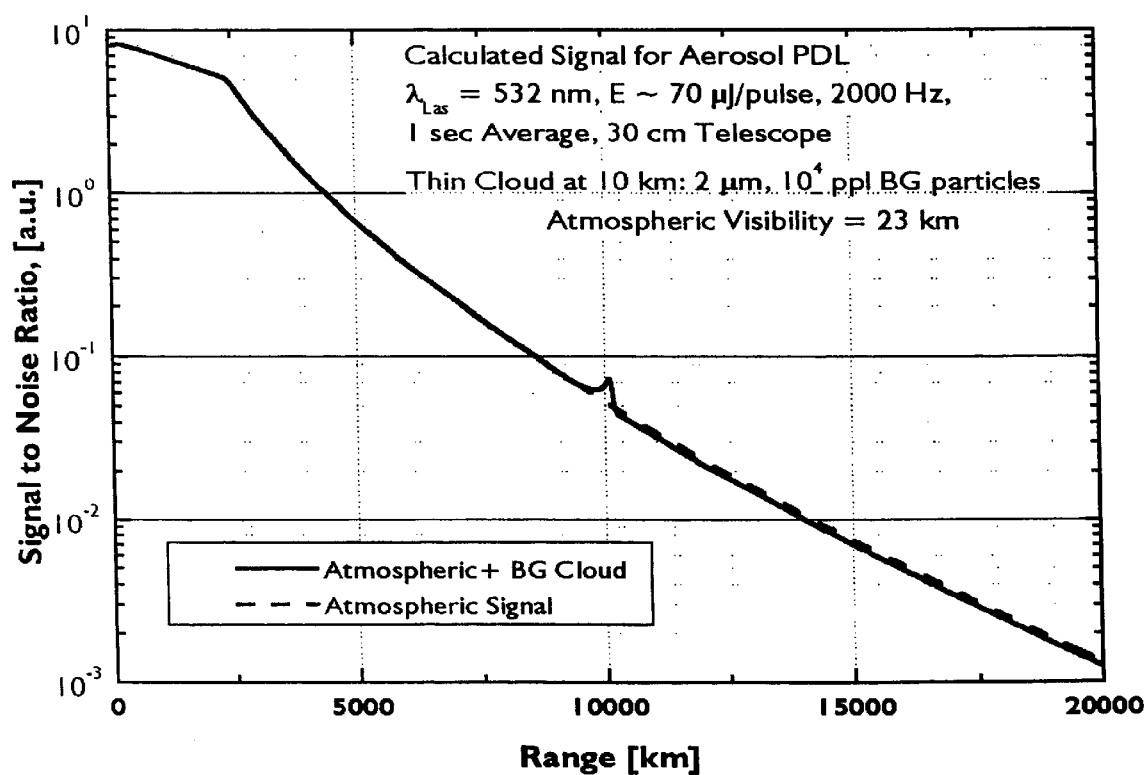

The backscattering coefficient $\beta_{BWA}$ from internal lidar measurements of simulants, as described previously in Hwang, et al, is estimated to be $4\times10^{-10}$/m. sr. particle for the BG simulant particles for $\lambda$=523 nm. This estimate is reasonable, because taking the mean size of the BG particles to be 2 $\mu$m, the backscattering cross-section of 2 $\mu$m dielectric spheres is of the same order of magnitude as the value obtained from our measurements. FIG. 7 shows the aerosol elastic backscatter signal as a function of the range. The laser energy is taken to be 70 $\mu$J/pulse such that the beam is eye-safe (see Table 3 of FIG. 10) after it is expanded to 30 cm dia in the telescope. The atmospheric extinction is calculated assuming a visibility of 23 km.

Figure 5:
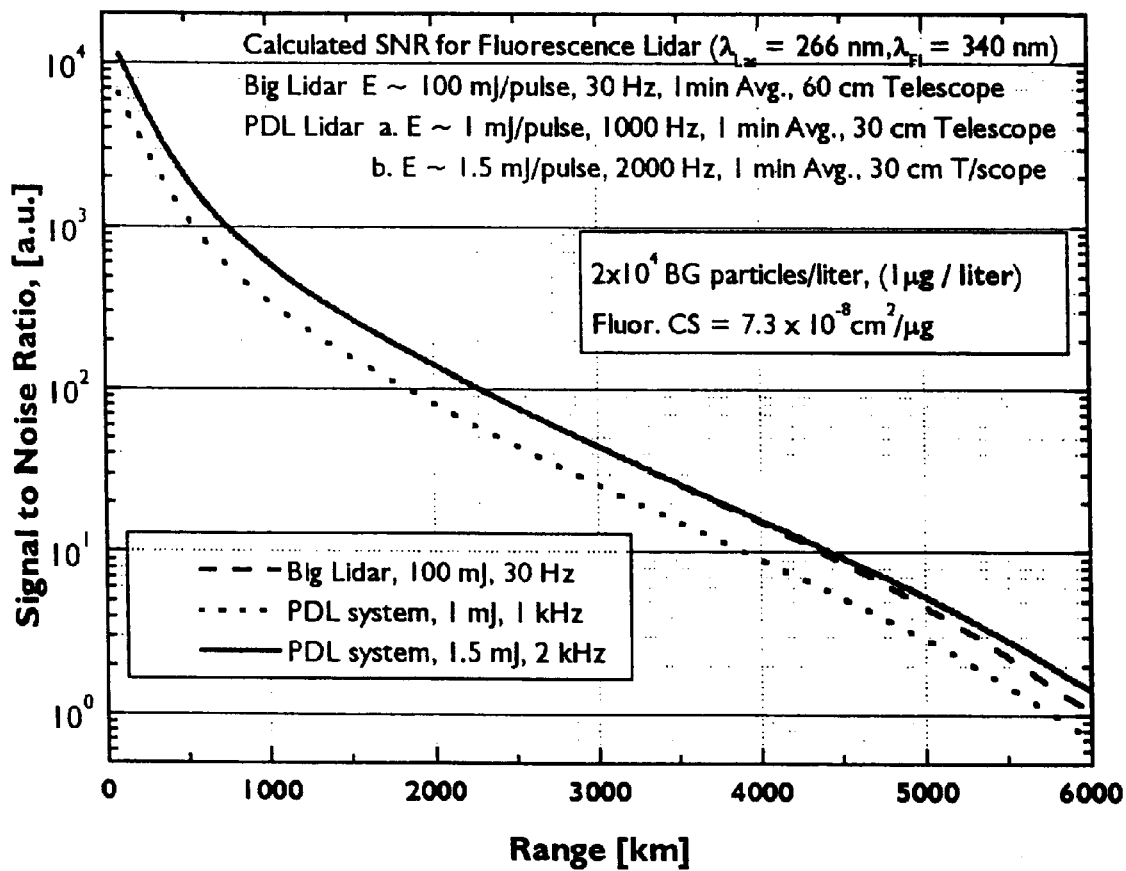
Figure 6:
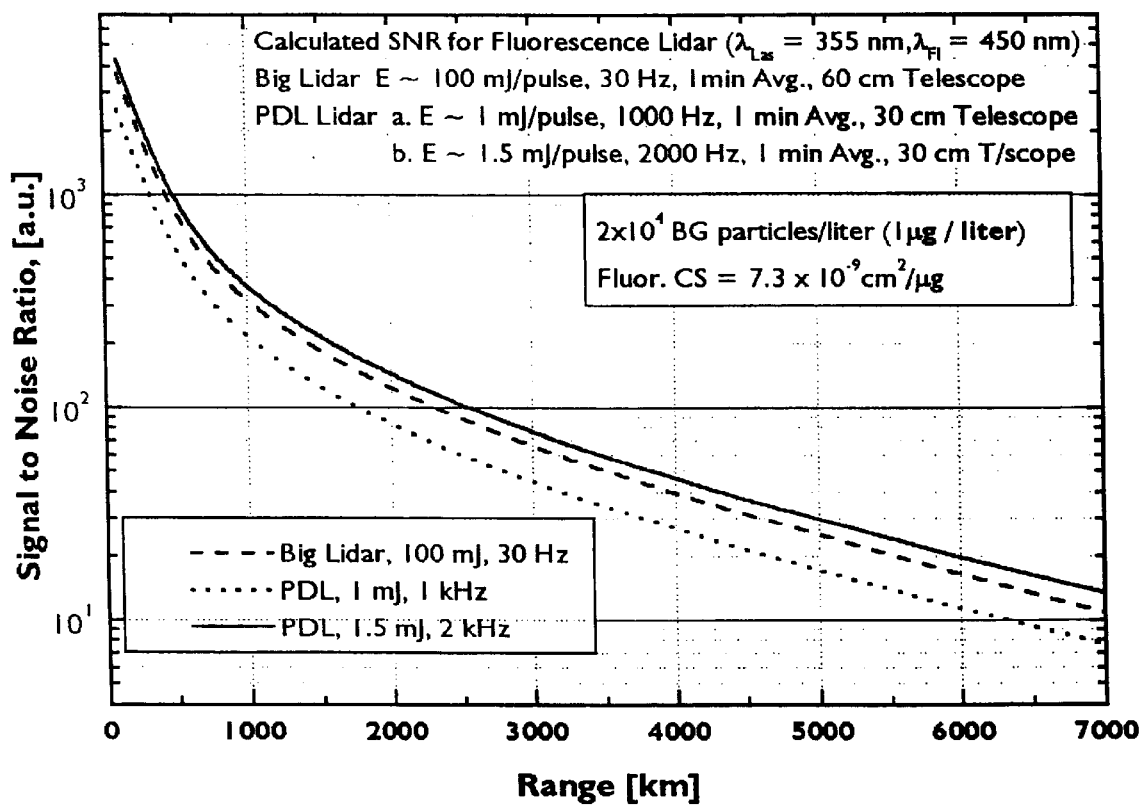

To prevent overloading the detector with the strong near field signal, geometric compression is incorporated in the form of a field stop (250 $\mu$m) at the focal point of the receiver optics. The size of the image formed by the telescope at its focus is a function of the range and reduces quadratically with the range until reaching the diffraction limit at a large range. By using a small pinhole, only a small part of the near field return signal falls on the detector. The image size becomes smaller than the 250 $\mu$m pinhole for range >3 km for the f/10 telescope. Thus, geometrical compression occurs for the first 2.5 km limiting the light falling on the detector and the full amount of signal subtended by the telescope aperture is transmitted through the aperture and received by the detector for the ranges beyond 2.5 km. In FIGS. 5, 6, and 7, the effect of geometric compression is shown for the near-field range where the signal is nearly flat.

FIG. 7 shows the SNR of the total signal (due to atmospheric aerosols and the BG aerosol) calculated using equation (1). When a cloud is detected, the signal due to the cloud is calculated by subtracting the atmospheric background signal from the total signal.

Thus, in general, the lidar system includes a laser 54 which provides laser pulses of at least two wavelengths, a transceiver optical module 51 including transmitter (shown as the lower half components in FIG. 3A) which transmits the laser pulses, a receiver (shown as the upper half components in FIG. 3A) which receives both elastically backscattered signals from airborne agents and fluorescence signals from the airborne agents, a common telescope 16 which both focuses a laser beam transmission of the laser pulse from the transmitter to a far field and receives the elastically backscattered signals and the fluorescence signals from the far field, a digital detection system 52 having at least one of a backscatter optical detector 17–19 which detects a presence of the airborne agents by detecting elastically backscattered signals and a fluorescence optical detector 20 which detects the fluorescence signals from the airborne agents.

The receiver is configured with a focal point 34 of the receiver located at a conjugate point of a focal point of the transmitter. The lidar system can include as shown in FIG. 4 a frame 60 which rigidly mounts optical components of the transmitter, the receiver, and the telescope and which maintains a predesignated direction of the laser beam transmission against vibration and shock of the system. Further, the lidar system can include an azimuthal and zenith scanning device 62 which scans by moving the laser system in an enclosure 64 supported on an axle and fork structure (not shown in FIG. 4).

The laser pulses can include at least one of a 1.06 micron wavelength pulse, a 525 nm wavelength pulse, and a 350 nm wavelength pulse. The laser can pulse (as shown in FIG. 8) with an energy of at least 1 mJ at the 350 nm wavelength pulse and at least hundred $\mu$J at the 1.06 micron wavelength pulse and the 525 nm wavelength pulse. The laser can pulse with a repetition rate of a 1–10 KHz. The transmitter is configured to transmit the laser pulses coaxially and to expand the laser pulses with the common telescope 16 such that the laser beam transmission is eye-safe.

The receiver includes an optical separator with a beam splitter 35 which separates the elastically backscattered signals and the fluorescence signal. The beam splitter 35 can include dichroic beam splitters to spit the elastically backscattered signals and the fluorescence signals. The transmitter in the transceiver optical module 51 can transmit a laser pulse in a 340 to 360 nm wavelength region to induce a fluorescence signal in a 440 nm wavelength region. The receiver can include an angular positioning device configured to position a focal point of the receiver to maximize the long-range return signal. This angular positioning device can be motorized and have position encoders for records.

The transmitter, the receiver, and the telescope can suppress light interference from internally scattered laser light through utilization of variable size apertures 31, 32, 33 which define a field of view at a focal point of the receiver and may be located at a maximum distance from sources of internal scatter to suppress light interference from internally scattered light. The transmitter can be configured to have a compressed dynamic range. Suppression of light interference in the present invention can be obtained by locating an optical baffle between the receiver and the backscatter optical detector or the fluorescence optical detector, by using a polarizing beam splitter 9, 15 or a rejection filter (e.g., a dichroic beam splitter located in front of the backscatter optical detector or the fluorescence optical detector), and by using high-grade UV optical components which minimize extraneous fluorescence that could be generated by laser light transmission through optical components such as for example, lenses with fluorescent optical bands.

In one embodiment of the present invention, the backscatter optical detector or the fluorescence optical detector can include an optical Q-switch in front of the detector to temporally filter the elastically backscattered signals and the fluorescence signals. The backscatter optical detectors 17–19 and the fluorescence optical detector 20 can utilize avalanche photodiode detectors such as for example a solid state Geiger mode detector. In another embodiment, an optical fiber matched by aperture size can couple a signal from a receiver focal point to the backscatter optical detector or the fluorescence optical detector.

The laser 54 can provide three wavelengths, i.e. a fundamental wavelength, a second harmonic wavelength, and a third harmonic wavelength. For example, the laser 54 could be a solid state laser such as a Nd:YAG laser, a Nd:YLF laser, a ND:YVO4 laser, and an Yb:YAG laser producing laser light at a fundamental wavelength of 1.064 $\mu$m, 1.047 or 1.053 $\mu$m, 1.064 $\mu$m, and 1.03 $\mu$m, respectively, a second harmonic wavelength of 532, 523 or 527, 532 and 515 nm, respectively, and a third harmonic wavelength of 355, 349 or 351, 355, and 343 nm, respectively. In one embodiment of the present invention, the laser can be tunable for differential lidar measurements of atmospheric trace gases. In another embodiment, the lidar system can include a Raman filter to resolve Raman scattering from specific atmospheric gases.

The lidar system of the present invention includes in the data acquisition system 50, a computer to analyze the backscattered signals to for example determine size distribution information, to analyze the fluorescence signals to determine an identity of the airborne agent, and to analyze the fluorescence signals to determine if the airborne agent is a bio-warfare agent. The computer can differentiate the bio-warfare agent by measuring multiple band fluorescence signals within a broad fluorescence band. The computer can differentiate naturally occurring aerosols from the bio-warfare agent by analyzing the elastically backscattered signals from laser pulses of at least three wavelengths. The computer can differentiate naturally occurring aerosols from the bio-warfare agent by analyzing information on a time evolution of a size of an aerosol cloud and a settling rate of the aerosol cloud. The computer can determine a wind speed and direction of the aerosol cloud by the size and settling rate of the aerosol cloud.

The computer can differentiate naturally occurring aerosols from the bio-warfare agent based on fluorescence signal data in conjunction with wavelength backscattering data from laser pulses of at least three wavelengths. The computer can differentiate naturally occurring aerosols from the bio-warfare agent by switching between a scanning mode to detect suspicious aerosol clouds at long-range and a non-scanning mode for high sensitivity fluorescence detection. The non-scanning mode utilizes fluorescence measurements in a single fluorescence filter band to provide a general indication of a presence of the bio-warfare agent in the suspicious aerosol cloud and utilizes multiple spectral bands for specific identification of the biological warfare agent or a class of biological warfare agents. The single fluorescence filter band may be restricted to a band 10 to 20 nm wide. The multiple spectral bands can include bands 2 to 5 nm wide.

This system represents a compact and robust aerosol and fluorescence portable digital lidar for stand-off detection and discrimination of biological and chemical-warfare agents is disclosed. The system utilizes digital detection to provide high sensitivity and excellent range capability. A single commercial laser whose energy requirements are modest (1.5 mJ at 355 nm, 0.35 mJ at 532 nm and 1 mJ at 1064 nm) is adequate. The resulting lidar system is low cost and robust for field use. Performance simulations by the present inventors have shown a better than 7 km range for the fluorescence lidar and a 20 km range for the aerosol lidar. Minimum detectable concentrations are ~1000 ppl at 2 km and 104 ppl at 4 km. These detectable concentrations agree closely with the results of other internal experiments by the present inventors where ~1300 ppl was obtained for 600 shot average at 1 km. By averaging over 10000 shots (only 5 seconds for the laser), the sensitivity improves to 325 ppl. Scanning at up to 5°/sec is possible so that a full sweep over a ±60° angular range can be accomplished in 48 seconds.

Hence, in one embodiment of the present invention, a method for detecting airborne agents (and corresponding means for detecting airborne agents) such as for example biological warfare gas agents includes the following steps (or means). At a first step, laser pulses of at least two wavelengths are transmitted through a transmission/reception device (e.g. the transceiver optical module 51. At a second step, elastically backscattered signals and fluorescence signals are received through a part of the transmission/reception device (e.g., a common telescope 16). At a third step, the presence of airborne agents is detected by analyzing differences in the elastically backscattered signals from the laser pulses of the at least two wavelengths. At a fourth step, the identity of the airborne agents is determined by analysis of the fluorescence signals.

Correspondingly, the first and second steps include aligning autonomously the telescope with transmitter and receiver optics in the transmission/reception device. The step of aligning autonomously can position a receiver field of view aperture at a conjugate point of a transmitter focal point across from a corresponding beamsplitter to maximize a reception of the elastically backscattered signals and the fluorescence signals from a far field.

The step of transmitting at the first step can pulse a laser with at least one of a 1.05 micron wavelength pulse, a 525 wavelength nm pulse, and a 350 nm wavelength pulse, can pulse with an energy of at least 1 mJ at the 350 nm wavelength pulse and pulse with an energy of at least a few hundred $\mu$J at the 1.05 micron wavelength pulse and the 525 nm wavelength pulse, can pulse with a repetition rate of 1–10 KHz.

Further, the step of transmitting at the first step can transmit the laser pulses coaxially and expand a laser beam of the laser pulses such that a laser beam transmission is eye-safe, can transmit a laser pulse in a 340 to 360 nm wavelength region to induce a fluorescence signal in a 440 nm wavelength region, can transmit a tunable laser pulse suitable for differential lidar measurements of atmospheric trace gases, and can steer the transmitted laser pulses by scanning in azimuthal and zenith directions.

The step of receiving at the second step can filter temporally the elastically backscattered signals and the fluorescence signal, can filter at least one of the elastically backscattered signals with a Raman filter to resolve Raman scattering measurements of specific atmospheric gases, can position a receiver field aperture at a focal point of the receiver to maximize a long-range return signal.

The steps of detecting and identifying at the third and fourth steps can analyze the elastically backscattered signals to determine size distribution information, can analyze the fluorescence signal to determine an identity of the airborne agent, can analyze the fluorescence signal to determine if the airborne agent is a bio-warfare agent, can differentiate the bio-warfare agent by measuring multiple band fluorescence signals within a broad fluorescence band, can differentiate naturally occurring aerosols from the bio-warfare agent by analyzing the elastically backscattered signals from laser pulses of at least three wavelengths, can differentiate naturally occurring aerosols from the bio-warfare agent by analyzing information on a time evolution of a size of an aerosol cloud and a settling rate of the aerosol cloud.

Further, the steps of detecting and identifying at the third and fourth steps can determine a wind speed and direction of the aerosol cloud by the size and the settling rate, can differentiate naturally occurring aerosols from the bio-warfare agent based on fluorescence signal data in conjunction with elastic backscattering data from laser pulses of at least three wavelengths, can differentiate naturally occurring aerosols from the bio-warfare agent by switching between a scanning mode to detect suspicious aerosol clouds at long-range and a non-scanning mode for high sensitivity fluorescence detection, and can differentiate naturally occurring aerosols from the bio-warfare agent by utilizing fluorescence measurements in a single fluorescent band to provide a general indication of a presence of the bio-warfare agent in the suspicious aerosol cloud and utilizes multiple spectral bands for specific identification of the biological warfare agent or a class of biological warfare agent.

Numerous modifications and variations of the present invention are possible in light of the above teachings. It is therefore to be understood that within the scope of the appended claims, the present invention may be practiced otherwise than as specifically described herein.

What is claimed as new and desired to be secured by Letters Patents of the United States is:

1. A system for detecting airborne agents, comprising:
   a laser configured to provide laser pulses of at least two wavelengths;
   a transmitter configured to transmit the laser pulses;
   a receiver configured to receive elastically backscattered signals and fluorescence signals from the airborne agents;
   a common telescope configured to focus a laser beam transmission of the laser pulses from the transmitter to a far field and to receive the elastically backscattered signals and the fluorescence signals from the far field; and
   a digital detection system, comprising at least one of,
      a backscatter optical detector configured to detect said elastically backscattered signals, and
      a fluorescence optical detector configured to detect the fluorescence signals from the airborne agents.

2. The system of claim 1, wherein the receiver has a focal point located at a conjugate point of a focal point of the transmitter.

3. The system of claim 2, further comprising:
   a frame configured to maintain at least one predesignated direction of the laser beam transmission in an environment where the system is subject to vibration and shock.

4. The system of claim 3, wherein the frame rigidly mounts optical components of the transmitter, the receiver, and the telescope.

5. The system of claim 3, wherein the receiver comprises a field of view aperture located at the focal point of the receiver and configured to maximize a long-range return signal.

6. The system of claim 1, wherein the laser pulses comprises at least one of a 1.05 micron wavelength pulse, a 525 nm wavelength pulse, and a 350 nm wavelength pulse.

7. The system of claim 6, wherein the laser is configured to pulse with an energy of at least 1 mJ at the 350 nm wavelength pulse and to pulse with an energy of at least a hundred $\mu J$ at the 1.06 micron wavelength pulse and the 525 nm wavelength pulse.

8. The system of claim 6, wherein the laser is configured to pulse with a repetition rate of 1 KHz–10 KHz.

9. The system of claim 1, wherein the transmitter is configured to transmit the laser pulses coaxially and to expand the laser pulses with the common telescope such that the laser beam transmission is eye-safe.

10. The system of claim 1, wherein the receiver comprises:
    an optical separator including a beam splitter and configured to separate the elastically backscattered signals and the fluorescence signal.

11. The system of claim 10, wherein the beam splitter comprises dichroic beam splitters configured to spit the elastically backscattered signals and the fluorescence signal.

12. The system of claim 1, wherein the transmitter transmits a laser pulse in a 340 to 360 nm wavelength region configured to induce a fluorescence signal in a 440 nm wavelength region.

13. The system of claim 1, wherein the transmitter, the receiver, and the telescope are configured to suppress light interference from internally scattered laser light.

14. The system of claim 13, wherein the receiver comprises a variable size aperture configured to define a field of view at a focal point of the receiver.

15. The system of claim 14, wherein the aperture is a field of view aperture located at a maximum distance from sources of internal scatter to the at least one wavelength laser pulse configured to suppress light interference from internally scattered light.

16. The system of claim 13, wherein the receiver comprises an optical baffle located between the receiver and at least one of the backscatter optical detector and the fluorescence optical detector.

17. The system of claim 13, wherein the beam splitter comprises a polarizing beam splitter.

18. The system of claim 17, wherein the receiver comprises:
    a rejection filter including a dichroic beam splitter, located in front of at least one of the backscatter optical detector and the fluorescence optical detector.

19. The system of claim 18, wherein optical components of the transmitter, the receiver, and the telescope are configured with high-grade UV optical components configured to minimize extraneous fluorescence from the optical components.

20. The system of claim 13, wherein at least one of the backscatter optical detector and the fluorescence optical detector include an optical Q-switch in front of the detector configured to temporally filter the elastically backscattered signals and the fluorescence signal.

21. The system of claim 1, wherein the transmitter is configured to have a compressed dynamic range.

22. The system of claim 1, wherein at least one of the backscatter optical detector and the fluorescence optical detector include an avalanche photodiode detector.

23. The system of claim 22, wherein the avalanche photodiode detector is a solid state Geiger mode detector.

24. The system of claim 1, further comprising:
    an optical fiber matched by aperture size and configured to couple a signal from a focal point of the receiver to at least one of the backscatter optical detector and the fluorescence optical detector.

25. The system of claim 1, wherein the laser provides laser pulses of three wavelengths.

26. The system of claim 25, wherein the solid state laser comprises at least one of a diode-pumped Nd:YAG laser, a diode-pumped Nd:YLF laser, a diode-pumped ND:YVO4 laser, and a diode-pumped Yb:YAG laser producing laser light at a fundamental wavelength of 1.064 $\mu m$, 1.047 or 1.053 $\mu$m, 1.064 $\mu$m, and 1.03 $\mu$m, respectively, a second harmonic wavelength of 532, 523 or 527, 532 and 515 nm, respectively, and a third harmonic wavelength of 355, 349 or 351, 355, and 343 nm, respectively.

27. The system of claim 1, wherein the laser is tunable for differential lidar measurements of atmospheric trace gases.

28. The system of claim 1, wherein the digital detection system includes a Raman filter for Raman scattering measurements of specific atmospheric gases.

29. The system of claim 1, further comprising:
a scanning device configured to scan in azimuthal and zenith directions by moving the system including said transmitter and said receiver in an enclosure supported on an axle and fork structure.

30. The system of claim 1, further comprising:
a computer configured to analyze the elastically backscattered signals to determine size distribution information.

31. The system of claim 30, wherein the computer is further configured to analyze the fluorescence signal to determine an identity of the airborne agent.

32. The system of claim 30, wherein the computer is further configured to analyze the fluorescence signal to determine if the airborne agent is a bio-warfare agent.

33. The system of claim 32, wherein the computer is configured to differentiate the bio-warfare agent by measuring multiple band fluorescence signals within a broad fluorescence band.

34. The system of claim 33, wherein the computer is configured to differentiate naturally occurring aerosols from the bio-warfare agent by analyzing the elastically backscattered signals from the laser pulses of the at least two wavelengths.

35. The system of claim 33, wherein the computer is configured to differentiate naturally occurring aerosols from the bio-warfare agent by analyzing information on a time evolution of a size of an aerosol cloud and a settling rate of the aerosol cloud.

36. The system of claim 35, wherein the computer is configured to determine a wind speed and direction of the aerosol cloud by said size and said settling rate.

37. The system of claim 33, wherein the computer is configured to differentiate naturally occurring aerosols from the bio-warfare agent based on fluorescence signal data in conjunction wavelength backscattering data from laser pulses of at least three wavelengths.

38. The system of claim 33, wherein the computer is configured to differentiate naturally occurring aerosols from the bio-warfare agent by switching between a scanning mode to detect suspicious aerosol clouds at long-range and a non-scanning mode for high sensitivity fluorescence detection.

39. The system of claim 38, wherein the non-scanning mode utilizes fluorescence measurements in a single fluorescent filter band to provide an indication of a presence of the bio-warfare agent in the suspicious aerosol clouds and utilizes multiple spectral bands for specific identification of the biological warfare agent or a class of biological warfare agents.

40. The system of claim 39, wherein the single fluorescence filter band comprises a band 10 to 20 nm wide.

41. The system of claim 39, wherein the multiple spectral bands comprise bands 2 to 5 nm wide.

42. A system for detecting and identifying airborne agents, comprising:

means for transmitting laser pulses of at least two wavelengths;

means for receiving elastically backscattered signals from the airborne agents and fluorescence signals from the airborne agents;

means for detecting a presence of the airborne agents by analyzing differences in the elastically backscattered signals from the laser pulse of at least two wavelengths, and means for identifying of the airborne agents by analyzing a fluorescence signal induced by transmitted laser pulses.

43. The system of claim 42, wherein said means for transmitting and said means for receiving utilize a common telescope.

44. The system of claim 43, further comprising:

means for aligning autonomously the system including said means for transmitting and said means for receiving.

45. The system of claim 44, wherein the means for aligning autonomously comprises:

means for positioning a receiver field of view aperture at the conjugate point of the transmitter focal point across the beam splitter to maximize a reception of the elastically backscattered signals and the fluorescence signals.

46. The system of claim 44, wherein the means for aligning autonomously comprises:

means for mounting transmitter and receiver optical components on a single optics board to withstand vibration and shocks encountered in field operations.

47. The system of claim 44, wherein the means for aligning autonomously comprises:

means for attaching the telescope, said means for transmitting, and said means for receiving to a rigid frame.

48. The system of claim 42, wherein the means for transmitting comprises:

means for pulsing a laser with at least one of a 1.05 micron wavelength pulse, a 525 nm wavelength pulse, and a 350 nm wavelength pulse.

49. The system of claim 48, wherein the means for pulsing comprises:

means for pulsing with an energy of at least 1 mJ at the 350 nm wavelength pulse and with an energy of at least a few hundred $\mu$J at the 1.05 micron wavelength pulse and the 525 nm wavelength pulse.

50. The system of claim 48, wherein the means for pulsing comprises:

means for pulsing with a repetition rate of 1–10 KHz.

51. The system of claim 42, wherein the means for transmitting comprises:

means for transmitting the laser pulses coaxially; and means for expanding the laser pulses such that a laser beam transmission is eye-safe.

52. The system of claim 42, wherein the means for transmitting comprises:

means for transmitting a laser pulse in a 340 to 360 nm wavelength region to induce a fluorescence signal in a 440 nm wavelength region.

53. The system of claim 42, wherein the means for receiving comprises:

means for filtering temporally the elastically backscattered signals and the fluorescence signal.

54. The system of claim 42, wherein the means for transmitting comprises:

means for transmitting a tunable laser pulse suitable for differential lidar measurements of atmospheric trace gases.

55. The system of claim 42, wherein the means for receiving comprises:
  means for filtering at least one of the elastically backscattered signals with a Raman filter to resolve a Raman scattering signal of a specific gas.

56. The system of claim 42, wherein the means for receiving comprises:
  means for positioning a receiver field stop to maximize a long-range return signal.

57. The system of claim 42, wherein the means for transmitting comprises:
  means for steering the transmitted laser pulses in azimuthal and zenith directions.

58. The system of claim 42, further comprising:
  means for analyzing the elastically backscattered signals to determine size distribution information.

59. The system of claim 42, further comprising:
  means for analyzing the fluorescence signal to determine an identity of the airborne agent.

60. The system of claim 42, further comprising:
  means for analyzing the fluorescence signal to determine if the airborne agent is a bio-warfare agent.

61. The system of claim 60, wherein the means for analyzing comprises:
  means for differentiating the bio-warfare agent by measuring multiple band fluorescence signals within a broad fluorescence band.

62. The system of claim 61, wherein the means for differentiating comprises:
  means for differentiating naturally occurring aerosols from the bio-warfare agent by analyzing the elastically backscattered signals from laser pulses of at least three wavelengths.

63. The system of claim 61, wherein the means for differentiating comprises:
  means for differentiating naturally occurring aerosols from the bio-warfare agent by analyzing information on a time evolution of a size of an aerosol cloud and a settling rate of the aerosol cloud.

64. The system of claim 63, wherein the means for analyzing comprises:
  means for determining a wind speed and direction of the aerosol cloud by said size and said settling rate.

65. The system of claim 61, wherein the means for differentiating comprises:
  means for differentiating naturally occurring aerosols from the bio-warfare agent based on fluorescence signal data in conjunction wavelength backscattering data from laser pulses of at least three wavelengths.

66. The system of claim 61, wherein the means for differentiating comprises:
  means for differentiating naturally occurring aerosols from the bio-warfare agent by switching between a scanning mode to detect suspicious aerosol clouds at long-range and a non-scanning mode for high sensitivity fluorescence detection.

67. The system of claim 61, wherein the means for differentiating comprises:
  means for differentiating naturally occurring aerosols from the bio-warfare agent by utilizing fluorescence measurements in a single fluorescent band to provide a general indication of a presence of the bio-warfare agent in the suspicious aerosol cloud and utilizes multiple spectral bands for specific identification of the biological warfare agent or a class of biological warfare agents.

* * * * *